United States Patent [19]

Bryant et al.

[11] Patent Number: 5,087,457
[45] Date of Patent: Feb. 11, 1992

[54] SYNERGISTIC MICROBICIDES CONTAINING IONENE POLYMERS AND BORATES FOR THE CONTROL OF FUNGI ON SURFACES

[75] Inventors: Stephan D. Bryant, Memphis, Tenn.; John Packer, Dorval; Thomas D. Johnstone, Montreal, both of Canada

[73] Assignee: Buckman Laboratories International, Inc., Memphis, Tenn.

[21] Appl. No.: 464,014

[22] Filed: Jan. 12, 1990

[51] Int. Cl.$^5$ .................. A01N 33/12; A01N 59/14
[52] U.S. Cl. .................. 424/78.37; 424/659; 424/660; 424/658; 514/642
[58] Field of Search .................. 424/78, 658, 659, 660; 514/642

[56] References Cited

U.S. PATENT DOCUMENTS

| | | | |
|---|---|---|---|
| 3,771,989 | 11/1973 | Pera et al. | 71/67 |
| 4,018,592 | 4/1977 | Buckman et al. | 71/67 |
| 4,054,542 | 10/1977 | Buckman et al. | 71/67 |
| 4,089,977 | 5/1978 | Green et al. | 260/567.6 |
| 4,111,679 | 9/1978 | Shair et al. | 71/67 |
| 4,140,798 | 2/1979 | Merianos et al. | 260/584 |
| 4,400,298 | 8/1983 | Boocock et al. | 424/658 |
| 4,506,081 | 3/1985 | Fenyes et al. | 544/372 |

FOREIGN PATENT DOCUMENTS 3613252 10/1987 Fed. Rep. of Germany ...... 424/659

OTHER PUBLICATIONS

Rembaum, A., "Biological Activity of Ionene Polymers," 22nd Applied Polymer Symposium, 299–317 (1973).
F. C. Kull, P. C. Eisman, H. D. Sylwestrowica, and R. L. Mayer, Applied Microbiology 9:538–541 (1961).

*Primary Examiner*—Allen J. Robinson
*Attorney, Agent, or Firm*—Finnegan, Henderson, Farabow, Garrett & Dunner

[57] ABSTRACT

A mixture of an ionene polymer and a borate that is useful for the control of fungi. This microbicidal mixture is especially effective on the surfaces of wood, leather, plastics, paint, paper and paperboard, and textiles.

3 Claims, No Drawings

SYNERGISTIC MICROBICIDES CONTAINING IONENE POLYMERS AND BORATES FOR THE CONTROL OF FUNGI ON SURFACES

The present invention relates to the control of fungi on surfaces. In particular, the present invention relates to a microbicidal mixture that is effective in the control of fungi.

BACKGROUND OF THE INVENTION

Fungi are plants which obtain their nutrition from a preformed organic carbon source. The body of the fungus (hyphae) secretes enzymes which degrade the organic substrate on which they are growing and yield smaller subunits. These in turn are absorbed into the body of the fungus whereby they are metabolized and the organism derives energy to carry on vital processes.

One such source of energy is raw, unseasoned wood produced from the activities of sawmills. The sawn logs represent a rich source of organic and inorganic compounds contained within a moist cellulosic matrix. Sawmills characteristically stack raw lumber outside in order to air dry (cure). During this relatively slow process of drying, the lumber is continuously being assaulted by fungal spores whose germination and growth on the wood surface may lead to significant economic loss to the sawmill as a result of surface disfigurement. In addition, other fungal species may reside on the wood which actually decay or diminish the structural integrity of the wood by enzymatically hydrolyzing the cellulose and/or lignin within the primary and secondary cell walls.

The lumber industry controls these fungal problems through the application of chemicals to the freshly sawn wood. Chemicals which have experienced widespread use in this industry, such as pentachlorophenol (PCP), 2-thiocyanomethylthiobenzothiazole (TCMTB), 3-iodo-propynylbutylcarbamate (IPBC), and disodium octaborate tetrahydrate (available commercially as Tim-Bor ®), also exhibit disadvantages.

For instance, the organic antifungal agents PCP, TCMTB, and IPBC have been the objects of increasing environmental concern and legal restrictions of usage relative to their alleged contamination of the environment as well as complaints related to worker exposure. The borates also have a major disadvantage in that they will leach from treated wood when the wood is exposed to water. The net result of this is to reduce the effective concentration of borate in the wood and compromise its fungistatic activity.

The bactericidal and fungicidal activities of ionene polymers are known and have been described by Rembaum, A., "Biological Activity of Ionene Polymers," 22nd Applied Polymer Symposium, 299-317 (1973). The microbicidal property of ionenes have been disclosed in U.S. Pat. Nos. 4,018,592, 3,771,989, 4,054,542, 4,506,081, 4,111,679, 4,089,977, and 4,140,798. The biocidal activities of ionenes, however, are greatly reduced in systems possessing negatively charged fibers such as those represented by pulp slurries and wood. Moreover, the fungicidal activity of ionene is relatively poor compared with their algicidal and bactericidal activities.

Wood preservative compositions containing borates and alkyl-ammonium type compounds have also been disclosed in Japanese Patent No. 58/189-104.

SUMMARY OF THE INVENTION

The present invention overcomes the problems of the prior art by providing a mixture that does not have the environmental problems of the organic antifungal agents, and does not experience the reduction in fungistatic activity from leaching to the extent that prior art borates experience. The present invention further provides a mixture which has improved fungicidal activity over ionenes alone. The present invention further provides a biocidal composition useful in treating freshly cut lumber to prevent and control the growth of microorganisms. Other advantages provided by the present invention are described below or are apparent from the description below.

The importance of this invention is derived from the much reduced environmental risk of two compounds, a water soluble ionene polymer and a water soluble borate, which, when mixed in certain proportions, provide a synergistic level of action (more than additive) in preventing fungal infestation of fresh cut lumber. This discovery represents a potentially important alternative to standard, more hazardous chemical treatments in the prevention of economic losses in the lumber industry caused by fungi.

The present invention comprises a mixture of:

(a) from 1-99 percent, by weight, of 60% ionene polymer; and (b) from 1-99 percent, by weight, of water soluble borate.

In a preferred embodiment, the present invention comprises a mixture of:

(a) from 1-99 percent, by weight, of 60% ionene polymer having the formula;

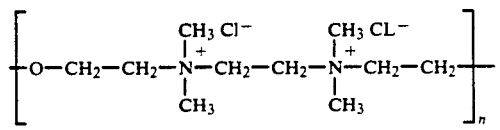

where n is an integer varying from 4 to 40 and;

(b) from 1-99 percent, by weight, of a water soluble borate selected from the group consisting of disodium octaborate tetrahydrate, sodium pyroborate decahydrate and boric acid.

DETAILED DESCRIPTION OF THE INVENTION

The word ionene is a generic term which applies to the polyammonium salt which is formed through the reaction of diamines with dihalides. Ionenes are polyelectrolytes with positively charged nitrogen atoms located in the backbone of a polymeric. The present invention involves a polymeric quaternary ammonium compound which as a class is distinct from the simpler, monomeric quats. The structure of the ionene of the present invention generally has the following formula:

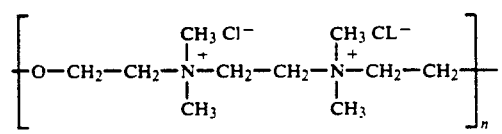

Where n is an integer varying from 4 to 40.

The preferred ionenes are (1) poly(oxyethylene(dimethyliminio)ethylene(dimethyliminio)ethylene dichloride, commercially available as WSCP; and poly(2-hydroxyethylenedimethyliminio-2-hydroxypropylenedimethyliminio methylene) dichloride, commercially available as APCA or Busan®1055.

Any water soluble borate can be used in the present invention. Preferred water soluble borates include disodium octaborate tetrahydrate, commercially available as Tim-Bor® and Other borates include boric acid.

The procedure for determining the biological activities of the individual components and their mixtures was conducted according to the procedure described by A. J. Cserjesi and J. W. Roff in "Accelerated Laboratory Test for Evaluating Toxicity of Fungicides for Lumber," Mater. Res. Stand. 10(3):18–19, 59–60 (1970) as follows.

The synergism of these two components is demonstrated by adding the ionene polymers (1) poly(oxyethylene(dimethyliminio)-ethylene(dimethyliminio)ethylene dichloride) (commercially available as WSCP), or (2) poly(2-hydroxyethylene-dimethyliminio-2-hydroxypropylene-dimethyliminio methylene) dichloride (commercially available as APCA or Busan® 1055), with either disodium octaborate tetrahydrate (known commercially as Tim-Bor ®) or sodium pyroborate decahydrate (known commercially as Borax ®). Other ionene and borates, including boric acid, should function similarly.

The ionene and the borate are mixed in varying ratios over a range of concentrations in water. These aqueous solutions were used to treat freshly cut pine sapwood coupons (3×5×0.3cm). The autoclaved coupons were individually immersed into the treatment solution with mild agitation for ten seconds and then placed horizontally on a screen in order to air dry for 24 hours.

Incubation units for the treated wood were prepared by inserting into sterile petri plates (10×5cm) a layer comprising four discs of moist, sterile Whatman 1 filter paper (7 cm diameter). Onto the paper was placed a sterile V-shaped glass rod which provided support for the wood coupon above the moist paper. The treated and dried coupon was placed on the glass rod, and the upper surface of the wood was inoculated with four drops of a freshly prepared spore suspension Aureobasidium pullulans, a common fungus which causes sapstain.

The covered petri dishes were incubated at 28° C. for two weeks at which time the wood treatments were evaluated based on the degree of fungal infestation. A score was given to treatments according to the following scheme:

0 - complex prevention of infestation
1 - very slight fungal infestation
2 - minor degree of infestation
3 - moderate infestation
4 - heavy infestation The lowest concentration of each compound or mixture required for complete prevention of sapstain was taken at the end point. In most cases, end points were not observed for individual compounds over the reasonable concentration range selected. End points for the mixtures of the compounds were then compared with the activities determined for the individual compounds acting alone. An end point is considered to be a score of 0 or 1.

Synergism was determined by the method described by F. C. Kull, P. C. Eisman, H. D. Sylwestrowica, and R. L. Mayer in Applied Microbiology 9:538–541 (1961) employing the ratio determined by:

$$QA/Qa + QB/Qb$$

wherein

Qa = percent of Compound A acting alone which produced an end point

Qb = solution percent of Compound B acting alone which produced an end point

QA = solution percent of Compound A in the mixture which produced an end point

QB = solution percent of Compound B in the mixture which produced an end point When the sum of QA/Qa and QB/Qb is greater than one, antagonism is indicated, and when the sum is equal to one, additivity is indicated. When the sum is less than one, synergism is demonstrated.

The concept of synergy may be illustrated further by reference to FIG. 1. This graph provides an example of the correlation between the chemical concentrations and interaction in minimal inhibitory concentration curves of a binary system. Although general and diagrammatic in nature, the graph instructs us that a particular desired effect, e.g., complete prevention of sapstain, may be achieved by a synergistic interaction of two chemicals. That is to say, the combination of two chemicals in a range of proportions at reduced levels will provide an effect which is achieved only at higher concentrations in an additive situation, or much higher concentrations for single components.

The data given in each of the four examples in this invention clearly describes a synergistic action between an ionene polymer and a borate in preventing sapstain on wood. In each example, this effect is achieved by the combination of the two chemicals at concentrations where either alone, or even at higher concentrations, is ineffective.

The procedure for demonstrating the synergism of the compositions of this invention is a widely used and accepted procedure. The present invention is demonstrated by the following examples. The examples address the following four mixtures:

| Ionene | Borate |
|---|---|
| 1. WSCP | Tim-Bor ® |
| 2. WSCP | Borax ® |
| 3. APCA | Tim-Bor ® |
| 4. APCA | Borax ® |

EXAMPLE 1

Synergism involving Compound A (WSCP, ionene polymer) and Compound B (Tim-Bor ®) was demonstrated by generating the data which appears in Table I.

TABLE I

| | | WSCP (% w/w) | | | |
|---|---|---|---|---|---|
| | | 0.0 | 1.0 | 2.0 | 4.0 |
| Tim-Bor ® | 0.0– | 4 | 4 | 4 | 4 |
| (% w/w) | 1.0– | 4 | 3 | 3 | 2 |
| | 2.0– | 4 | 2 | 2 | 1 |
| | 4.0– | 4 | 1 | 1 | 0 |

The evaluations given in Table I range from 4 (=heavy fungal/stain infestation) to 0 (=no apparent fungal stain or growth). In applying the scores to the Kull technique for identifying a synergism, it was necessary to use the mathematical symbols ">" (greater than) and "<" (less than). This was a result of not attempting to determine precisely the end points for individual compounds by using such excessively high concentrations. Those levels would be well beyond the range of practicality.

The demonstration of fungicidal effectiveness by the mixture at concentrations well below the level at which either component alone would be effective against the fungi is consistent with the concept of synergism. When the data was applied to the formula of Kull, et al., the following factors were derived:

$$Qa > 4.0 \quad Qb > 4.0$$
$$QA = 1.0 \quad QB = 2.0$$

Neither Compound A nor Compound B alone provided any significant anti-sapstain activity up to and including a 4% (w/w) solution. Thus, $$\begin{aligned} QA/Qa + QB/Qb &= 1.0/>4.0 + 2.0/>4.0 \\ &= <0.25 + <0.5 \\ &= <0.75 \end{aligned}$$

Since the sum of the ratios is less than 1.0, synergism is demonstrated.

EXAMPLE 2

Synergism Between Compound A (WSCP) and Compound B (Borax ®) was demonstrated by generating the data which appears in Table II.

TABLE II

|  |  | WSCP (% w/w) | | | |
|---|---|---|---|---|---|
|  |  | 0.0 | 0.62 | 1.25 | 2.5 |
| Borax ® | 0.0– | 4 | 4 | 4 | 4 |
| (% w/w) | 0.5– | 4 | 0 | — | — |
|  | 1.0– | 4 | — | 0 | — |
|  | 2.0– | 3 | — | — | 0 |

The biological activity results shown in Table II provided the following factors when evaluated by the Kull formula:

$$Qa > 2.5 \quad Qb > 2.0$$
$$QA = 0.62 \quad QB = 0.5$$

Thus $$\begin{aligned} QA/Qa + QB/Qb &= 0.62/>2.5 + 0.5/>2.0 \\ &= <0.25 + <0.25 \\ &= <0.50 \end{aligned}$$

Since the sum of the ratios is less than 1.0, synergism is demonstrated.

EXAMPLE 3

Synergism between a second ionene polymer commercially available as Busan ® 1055 or APCA (compound A) and Tim-Bor ® (compound B) was demonstrated by generating the dta which appears in Table III

TABLE III

|  |  | Busan ® 1055 (% w/w) | | | |
|---|---|---|---|---|---|
|  |  | 0.0 | 0.75 | 1.5 | 3.0 |
| Tim-Bor ® | 0.0– | 4 | 4 | 4 | 4 |
| (% w/w) | 0.75– | 4 | 3 | 1 | 1 |
|  | 1.5– | 4 | 0 | 0 | 0 |
|  | 3.0– | 0 | 0 | 0 | 0 |

The results shown in Table III demonstrate that the ionene polymer Busan ® 1055 was completely ineffective in preventing sapstain by itself in concentrations up to and including a 3.0% solution. Time-Bor ® was active at a concentration of no less than 3.0% in completely preventing sapstain. However, a treatment solution which was 0.75% Busan ® 1055 plus 1.5% Time-Bor ® was effective in total prevention of sapstain. When the data are applied to the formula of Kull, et al., the following factors are derived:

$$Qa > 3.0 \quad Qb = 3.0$$
$$QA = 0.75 \quad QB = .75$$

Therefore,
$$\begin{aligned} QA/Qa + QB/Qb &= 0.75/(>3.0) + (.75)/3.0 \\ &= (<0.25) + 0.25 \\ &< 0.5 \end{aligned}$$

A synergism between Busan ® 1055 and Tim-bor ® is demonstrated because the sum of the ratios provided by the Kull formula is less than 1.0.

EXAMPLE 4

Synergism involving the ionene polymer Busan ® 1055 (compound A) and Borax ® (compound B) was demonstrated by generating the data which appears in Table IV.

TABLE IV

|  |  | Busan ® 1055 (% w/w) | | | |
|---|---|---|---|---|---|
|  |  | 0.0 | 0.75 | 1.5 | 3.0 |
| Tim-Bor ® | 0.0– | 4 | 3 | 3 | 2 |
| (% w/w) | 0.5– | 4 | 3 | 3 | 2 |
|  | 1.0– | 4 | 1 | 0 | 0 |
|  | 2.0– | 0 | 0 | 0 | 0 |

When these data are applied to the formula of Kull et al., the following factors are generated:
Qa>3.0
QA=0.75
Qb=2.0
QB=1.0

The calculation of the ratios yields the following results:

$$\begin{aligned} QA/Qa + QB/Qb &= 1.5/>3.0 + 1.0/2.0 \\ &= <0.5 + 0.5 \\ &= <1.0 \end{aligned}$$

It is concluded from the results shown in Table IV that a synergism is demonstrated between Busan ® 1055 and Borax ® since the data when applied to the Kull formula for the microbicidal synergism, yield a net result of less than 1.0.

The microbicidal mixture of the present invention is effective in the control of fungi on a variety of surfaces. Some exemplary surfaces include wood, leather, plastics, paint, paper and paperboard, and textiles.

One of ordinary skill in the art will be aware that the above examples can be varied and modified and the invention is not intended to be limited to those examples, but only limited by the appended claims and their equivalents.

What is claimed is:

1. A microbicidal mixture effective in the control of fungi which comprises a synergistically effective mixture of an ionene polymer selected from the group consisting of poly(oxyethylene(dimethyliminio)ethylene(dimethylimino)ethylene dichloride) and poly(2-hydroxyethylenedimethylimino-2-hydroxypropylene-dimethylimino methylene) dichloride with a water soluble borate selected from the group consisting of disodium octaborate tetrahydrate, boric acid, and sodium pyroborate decahydrate.

2. A method for preventing the growth of fungi on surfaces comprising contacting said surfaces with a synergistically effective mixture of an ionene polymer selected from the group consisting of poly(oxyethylene(dimethylimino)ethylene(dimethyliminioethylene dichloride) and poly(2-hydroxyethylenedimethylimino-2-hydroxypropylene-dimethylimino methylene) dichloride with a water soluble borate selected from the group consisting of disodium octaborate tetrahydrate, boric acid, and sodium pyroborate decahydrate.

3. The method of claim 2 where said surface is selected from the group consisting of wood, leather, plastics, paint, paper or paperboard, and textiles.

* * * * *

UNITED STATES PATENT AND TRADEMARK OFFICE
CERTIFICATE OF CORRECTION

PATENT NO. : 5,087,457
DATED : February 11, 1992
INVENTOR(S) : Stephan D. Bryant et al.

It is certified that error appears in the above-identified patent and that said Letters Patent is hereby corrected as shown below:

Col. 7, claim 1, line 12, "dimethylimino" should read --dimethyliminio--; and lines 12-13, "(2-hydroxyethy-lenedimethylimino" should read --(2-hydroxyethylenedimethyliminio--.

Claim 2, column 8, line 7, "dimethylimino" should read --dimethyliminio--, and "(dimethyliminioethy-" should read --dimethyliminio) ethy- --.

Signed and Sealed this

Twenty-fourth Day of August, 1993

Attest:

BRUCE LEHMAN

Attesting Officer

Commissioner of Patents and Trademarks